United States Patent
Gale et al.

(10) Patent No.: US 10,307,218 B2
(45) Date of Patent: Jun. 4, 2019

(54) STEREOTACTIC GUIDE ASSEMBLIES AND METHODS OF USING SAME

(71) Applicant: THE CLEVELAND CLINIC FOUNDATION, Cleveland, OH (US)

(72) Inventors: John T. Gale, Chardon, OH (US); Jorge Gonzalez-Martinez, University Heights, OH (US); Shawan J. Anthony, Beachwood, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 587 days.

(21) Appl. No.: 14/989,342

(22) Filed: Jan. 6, 2016

(65) Prior Publication Data

US 2016/0193008 A1    Jul. 7, 2016

Related U.S. Application Data

(60) Provisional application No. 62/100,208, filed on Jan. 6, 2015.

(51) Int. Cl.
| | | |
|---|---|---|
| *A61N 1/05* | (2006.01) | |
| *A61M 27/00* | (2006.01) | |
| *A61B 90/10* | (2016.01) | |
| *A61B 90/11* | (2016.01) | |
| *A61B 90/00* | (2016.01) | |

(52) U.S. Cl.
CPC ............. *A61B 90/10* (2016.02); *A61B 90/11* (2016.02); *A61M 27/006* (2013.01); *A61N 1/0529* (2013.01); *A61B 2090/103* (2016.02); *A61B 2090/376* (2016.02)

(58) Field of Classification Search
CPC ... A61B 2090/103; A61B 90/10; A61B 90/11; A61M 27/006
See application file for complete search history.

(56) References Cited

U.S. PATENT DOCUMENTS

| | | | | |
|---|---|---|---|---|
| 4,265,252 A | * | 5/1981 | Chubbuck | A61B 5/031 600/561 |
| 5,927,277 A | | 7/1999 | Baudino et al. | |
| 7,048,716 B1 | | 5/2006 | Kucharczyk et al. | |

(Continued)

FOREIGN PATENT DOCUMENTS

| | | |
|---|---|---|
| DE | 10065799 C1 | 4/2002 |
| WO | 9629953 A1 | 10/1996 |
| WO | 03039386 A1 | 5/2003 |

OTHER PUBLICATIONS

PCT International Search Report and Written Opinion for PCT/US2016/012321, dated Apr. 21, 2016, pp. 1-11.

*Primary Examiner* — Leslie R Deak
(74) *Attorney, Agent, or Firm* — Tarolli, Sundheim, Covell & Tummino LLP

(57) ABSTRACT

One aspect of the present disclosure relates to a stereotactic guide assembly comprising an implantable body and a fastener. The implantable body can have an interior chamber and a first passageway that extends through the implantable body into communication with the interior chamber. At least a portion of the interior chamber can be defined by a first coupling feature. The fastener can be configured to fit in the interior chamber. The fastener can have a second passageway extending therethrough, and a second coupling feature adapted to releasably engage the first coupling feature.

14 Claims, 16 Drawing Sheets

(56) References Cited

U.S. PATENT DOCUMENTS

| | | |
|---|---|---|
| 7,235,084 B2 | 6/2007 | Skakoon et al. |
| 8,747,419 B2 * | 6/2014 | Solar ............... A61B 90/11 |
| | | 606/130 |
| 9,366,017 B2 * | 6/2016 | Cook ............... E03F 5/0408 |
| 2002/0049451 A1 | 4/2002 | Parmer et al. |
| 2009/0112327 A1 * | 4/2009 | Lane ............... A61N 1/0539 |
| | | 623/17.19 |
| 2013/0096570 A1 | 4/2013 | Solar et al. |

* cited by examiner

STEREOTACTIC GUIDE ASSEMBLIES AND METHODS OF USING SAME

RELATED APPLICATION

This application claims the benefit of U.S. Provisional Patent Application Ser. No. 62/100,208, filed Jan. 6, 2015, the entirety of which is hereby incorporated by reference for all purposes.

TECHNICAL FIELD

The present disclosure generally relates to systems and methods for guiding the implantation of medical devices intra-cerebral target sites and, in particular, to stereotactic guide assemblies and related methods that facilitate precision stereotactic targeting with image-guided technologies that reduce the time and cost associated with surgical revisions.

BACKGROUND

Stereotactic surgery is a minimally invasive form of surgical intervention that uses a three-dimensional (3D) coordinate system to locate intra-cerebral target sites to perform various surgical procedures. Frame-based stereotactic surgery uses a head frame that place the head of a subject in a fixed position with reference to the 3D coordinate system. Surgical instruments that attach to the head frame can be adjusted to the 3D coordinates of the target site so that the target site is accurately approached by the surgeon. Frameless stereotactic surgery relies on fiducial markers that are adhered to the subject's scalp before the brain is imaged. In the operating room, the orientation of these markers is used to register a computer containing certain brain images. Once registration is completed, the computer shows the relationship between the surgical instruments and the imaged brain.

Whether using a frame-based or frameless approach, an incision may be made in the scalp to expose the patient's skull once the target site has been accurately located. After forming a burr hole in the skull, a medical device can be inserted into the subject's brain and implanted at the target site. If a surgical revision is necessary, the indwelling medical device has to be removed and the trajectory reassessed for implanting a medical device at the target site again. Such a process is time consuming and costly.

SUMMARY

One aspect of the present disclosure relates to a stereotactic guide assembly comprising an implantable body and a fastener. The implantable body can have an interior chamber and a first passageway that extends through the implantable body into communication with the interior chamber. At least a portion of the interior chamber can be defined by a first coupling feature. The fastener can be configured to fit in the interior chamber. The fastener can have a second passageway extending therethrough, and a second coupling feature adapted to releasably engage the first coupling feature.

Another aspect of the present disclosure can relate to a stereotactic guide assembly comprising an implantable body and a fastener. The implantable body can have an interior chamber and a first passageway that extends through the implantable body into communication with the interior chamber. A first end portion of the first passageway can be defined by an external coupling feature. The fastener can be configured to fit in the interior chamber. The fastener can have a second passageway extending therethrough, and an internal coupling feature adapted to releasably engage the external coupling feature.

Another aspect of the present disclosure can relate to a method for implanting a first medical device in a target site of a subject's brain. One step of the method can include drilling a burr hole in a cranium of the subject. An implantable body can be inserted into the burr hole. The implantable body can have an interior chamber and a first passageway that extends through the implantable body into communication with the interior chamber. At least a portion of the interior chamber can be defined by a first coupling feature. Next, a first medical device can be advanced through the first passageway of the implantable body to the target site. A second coupling feature of a fastener can then be mated with the first coupling feature of the implantable body to secure the first medical device in place. A cover can be placed over the burr hole in the skin of the subject to cover the burr hole and the implantable body.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1A:
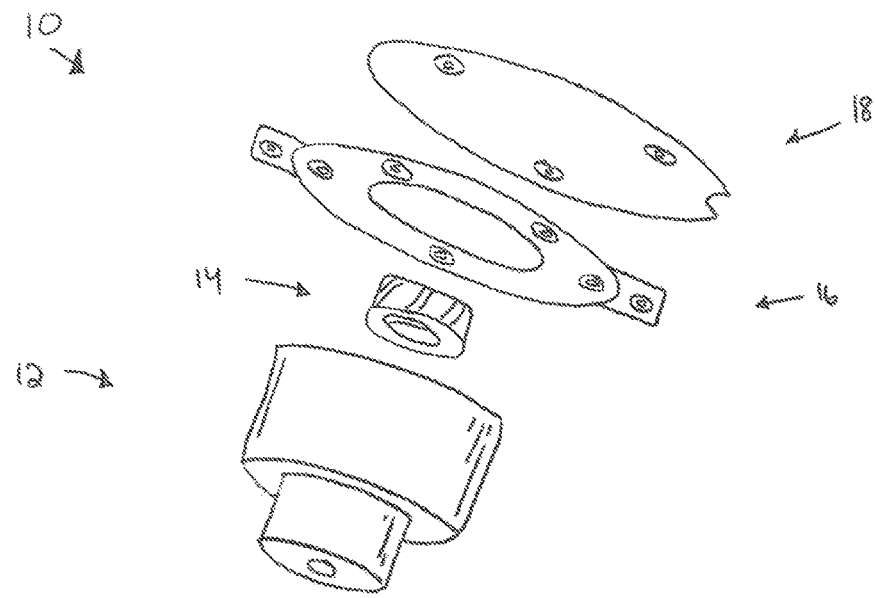
FIG. 1A is an exploded view of a stereotactic guide assembly constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "subject" and "patient" can be used interchangeably and refer to any warm-blooded organism including, but not limited to, human beings, pigs, rats, mice, dogs, goats, sheep, horses, monkeys, apes, rabbits, cattle, etc.

Overview

The present disclosure generally relates to systems and methods for guiding the implantation of medical devices intra-cerebral target sites and, in particular, to stereotactic guide assemblies and related methods that facilitate precision stereotactic targeting with image-guided technologies that reduce the time and cost associated with surgical revisions. The present disclosure combines instrumentation for implanting medical devices at a target site and an indwelling device that remains in the cranium of a subject after the medical device has been implanted. Advantageously, systems and methods of the present disclosure can eliminate the need for a stereotactic frame to determine the three-dimensional coordinates of a target site if a subsequent medical device is to be inserted into the target site, thereby permitting repeated target access while maintaining chronic stereotactic accuracy.

Stereotactic Guide Assemblies

One aspect of the present disclosure can include a stereotactic guide assembly comprising an implantable body and a fastener. The stereotactic guide assembly can be sized and dimensioned to fit within a burr hole located in a cranium of a subject. The implantable body can have an interior chamber and a first passageway that extends through the implantable body into communication with the interior chamber. At least a portion of the interior chamber can be defined by a first coupling feature. The fastener can be configured to fit in the interior chamber. The fastener can have a second passageway extending therethrough and a second coupling feature adapted to releasably engage the first coupling feature.

In some instances, the stereotactic guide assembly can further comprise a cranial fixation ring that is adapted to mate with the implantable body and thereby secure the implantable body within the burr hole. The cranial fixation ring can further comprise a guide portion and a plurality of radially spaced apart attachment members. The guide portion can be adapted to mate with an upper surface of the implantable body. Each of the attachment members can be connected to the guide portion and adapted to contact separate portions of the subject's cranium located adjacent the burr hole.

In further instances, the stereotactic guide assembly can include a cover that is sized and dimensioned to cover the implantable body when the implantable body is implanted in the burr hole. The cover can include a rim having a notch adapted to receive a medical device, such as an electrical lead, a catheter, a cannula, a stylet, a needle, and/or any other indwelling medical device.

It will be appreciated that the stereotactic guide assembly can be provided separately or as part of a pre-packaged surgical kit. A pre-packaged surgical kit can include other surgical components needed for operation of the stereotactic guide assembly, such as various drill bits, puncture tools, scalpels, adjustment tools and fasteners (e.g., screws, clips, staples, etc.), as well as instructions for use.

Figure 1B:
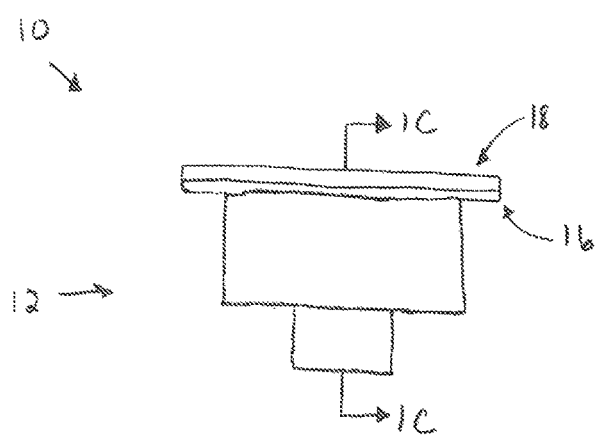
FIG. 1B is an assembled view of the stereotactic guide assembly in FIG. 1A.
Figure 1C:
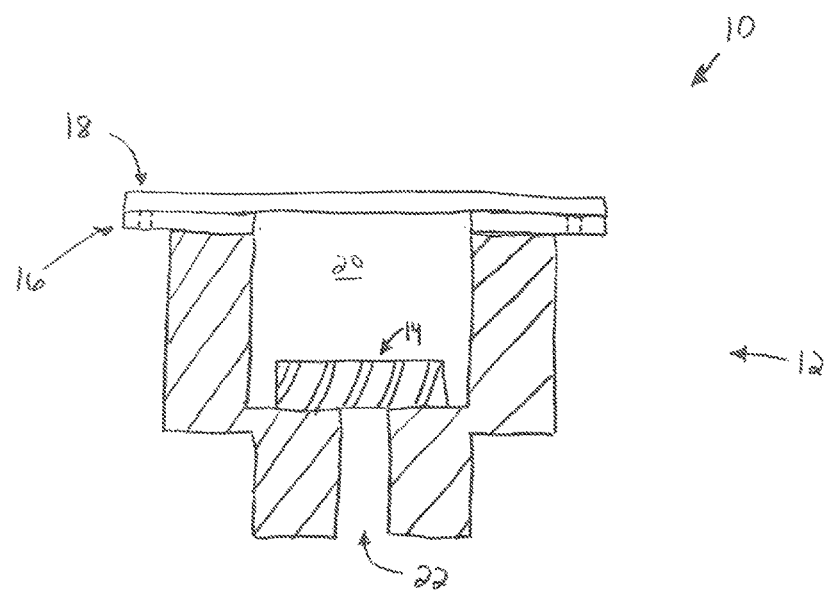
FIG. 1C is a cross-sectional view taken along Line 1C-1C in FIG. 1B.

In one example of the present disclosure, a stereotactic guide assembly 10 (FIGS. 1A-C) can comprise an implantable body 12, a fastener 14, a cranial fixation ring 16, and a cover 18. The implantable body 12 can be sized and dimensioned to fit within a burr hole located in the cranium of a subject. The implantable body 12 can include an interior chamber 20 and a first passageway 22 that extends through the implantable body into communication with the interior chamber. The first passageway 22 permits passage of various medical devices therethrough (e.g., during stereotactic surgery). The implantable body 12 can have a uniform diameter or a stepped-down configuration (as shown in FIGS. 1A-C) to fit within a counterbore drilled in the cranium of a subject. In the stepped-down configuration, the implantable body can comprise an upper portion 24 connected to a lower portion 26. In some instances, an outer diameter of the upper portion 24 can be greater than an outer diameter of the lower portion 26. In one example, the outer diameter of the upper portion 24 can be about 8 mm to about 13 mm (e.g., about 10 mm), and the outer diameter of the lower portion 26 can be about 3 mm to about 7 mm (e.g., about 5 mm). It will be appreciated that other configurations of the implantable body 12 are possible, such as a frusto-conical configuration.

The implantable body 12 can be made of a polymeric material. Advantageously, this construction allows the dimensions of the implantable body 12 to be shaped on-demand (e.g., at the time of implantation, during surgical planning, and/or during a surgical procedure) where the size of the implantable body needs to be optimized (e.g., based on the size of the burr hole and/or the anatomy of the patient). It will be appreciated that all or only a portion of the implantable body 12 can additionally or optionally be made of a metal and/or metal alloy. In some instances, the implantable body 12 can include an upper receiving surface 28 (FIG. 2B) configured to directly contact a portion of the cranial fixation ring 16 (FIGS. 1A-C). During a surgical procedure, for example, a medical professional can reduce the length of the upper portion 24 of the implantable body 12 by removing material from the upper receiving surface 28 (e.g., by sanding or shaving the surface) so that the implantable body optimally fits within a burr hole. Additionally or alternatively, other portions of the implantable body 12 can be shaped in an on-demand setting to ensure that the implantable body is optimally sized for implantation.

Figure 2A:
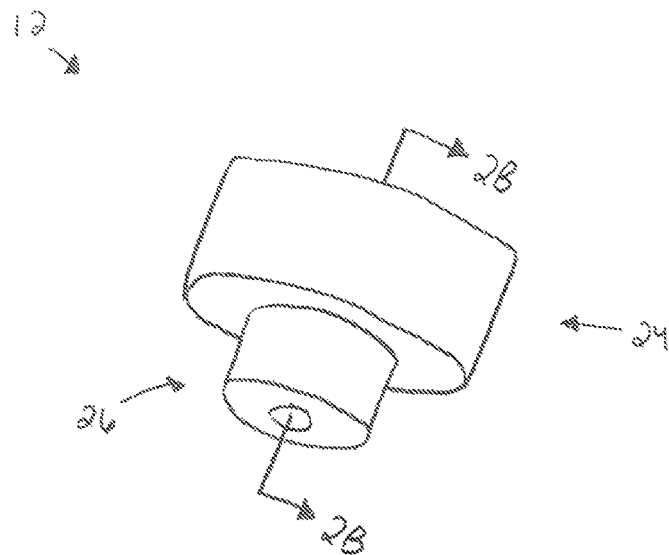
FIG. 2A is a perspective view showing an implantable body comprising the stereotactic guide assembly in FIGS. 1A-C.
Figure 2B:
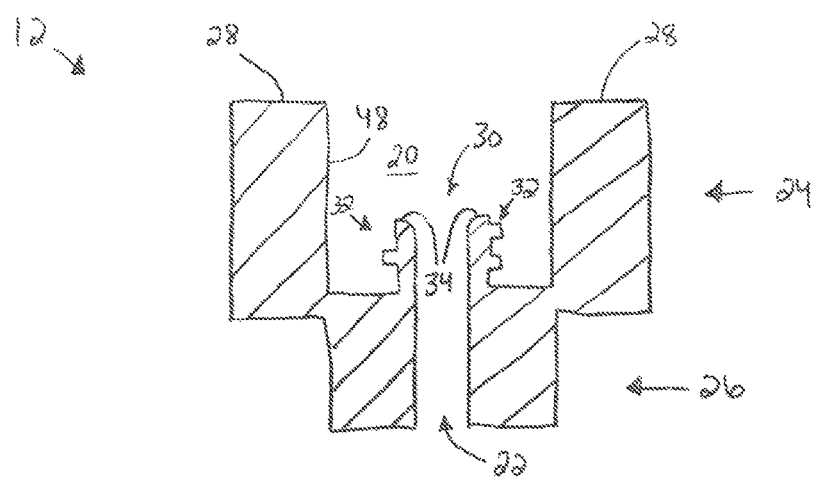
FIG. 2B is a cross-sectional view taken along Line 2B-2B in FIG. 2A.
Figure 3:
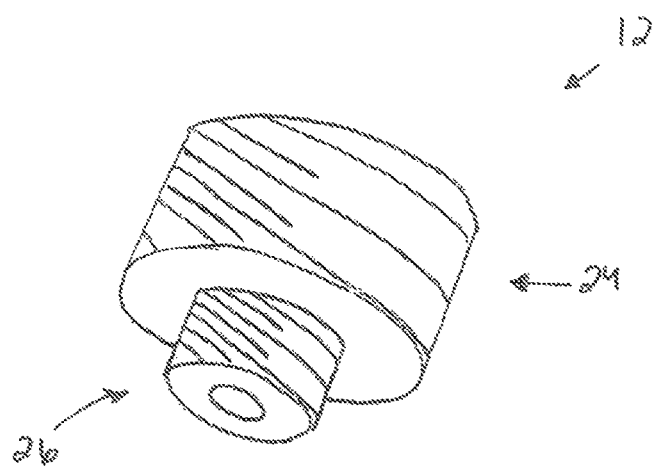
FIG. 3 is a perspective view showing an alternative construction of the implantable body in FIGS. 2A-B.

Referring to FIGS. 2A-B, a first end portion 30 of the first passageway 22 can be defined by an external coupling feature 32. In one example, the external coupling feature 32 can comprise a cannulated cylinder having an externally threaded section. The external coupling feature 32 can also include a beveled edge 34 to facilitate insertion of a medical device into the first passageway 22. It will be appreciated that, in some instances, each of the upper and lower portions 24 and 26 of the implantable body 12 can be externally threaded. As shown in FIG. 3, this configuration allows the implantable body 12 to be threaded into a burr hole without the need for the cranial fixation ring 16. In such instances, the implantable body 12 can be fabricated from a metallic or semi-metallic material, such as titanium or stainless steel.

Figure 4A:
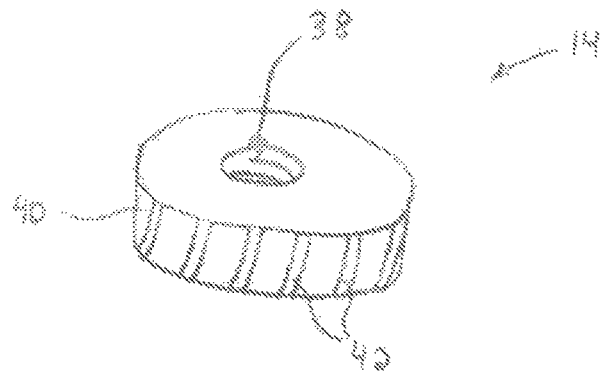
FIG. 4A is a perspective view of a fastener comprising the stereotactic guide assembly in FIGS. 1A-C.
Figure 4B:
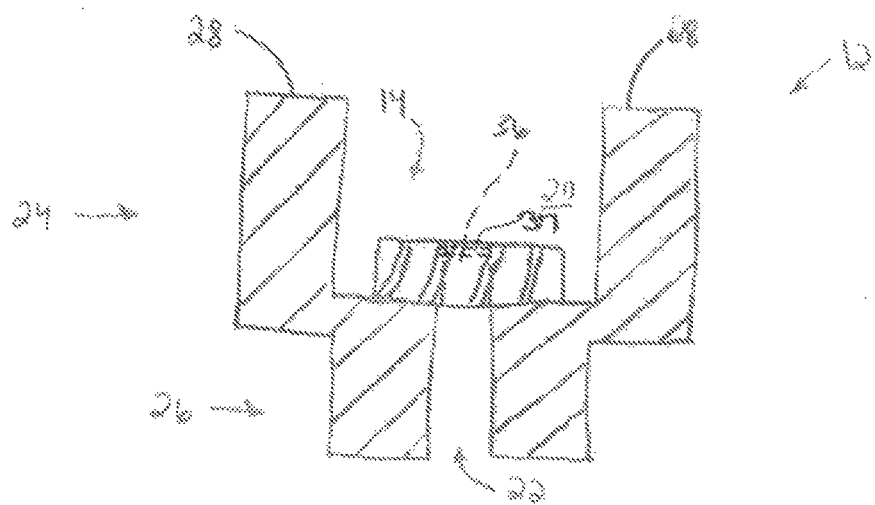
FIG. 4B is a cross-sectional view showing the fastener in FIG. 4A seated within the implantable body of FIG. 2B.

The stereotactic guide assembly can further include a fastener 14 (FIGS. 4A-B) configured to fit in the interior chamber 20 of the implantable body 12. The fastener 14 serves to lock a medical device in place. In one example, the fastener 14 can be ring-shaped and have a second passageway 36 extending therethrough. The fastener 14 also includes an internal coupling feature 38 adapted to releasably engage the external coupling feature 32. In some instances, the internal coupling feature 38 can comprise a threaded section that is complementary to the threaded section of the external coupling feature 32. It will be appreciated that the external coupling feature 32 and the internal coupling feature 38 can releasably engage one another other via other mechanisms, such as a male-female fastening mechanism, a snap-fit, a friction-fit, an interference-fit, or screwing the fastener 14 to the top of the implantable body 12 (which forms a compression connection). Advantageously, the fastener 14 is configured to releasably couple with (or engage) the implantable body 12, which enables a medical practitioner to exchange various instrumentation with the stereotactic guide assembly 10 without having to use a stereotactic frame each time a different medical device or instrument is needed for insertion into the brain of a subject.

To facilitate removal of the fastener 14 from the implantable body 12, the fastener can have an outer surface 40 comprising one or more ridges 42. The ridges 42 can be adapted to mate with a tool (not shown) that can be inserted into the implantable body 12 and configured to grasp the fastener 14 (e.g., to adjust or remove the fastener). The fastener 14 can have other features, such as protrusions, grooves, indentations, and the like, so long as a portion of the fastener can mate with the tool. To seal a medical device that has been inserted into the implantable body 12, the second passageway 36 of the fastener 14 can include a sealing ring 37 securely disposed therein. The sealing ring can be fabricated from an elastomeric or rubber material, for example, so that the sealing ring snugly contacts the inserted medical device and thereby seals or fixes the medical device in place.

Figure 5:
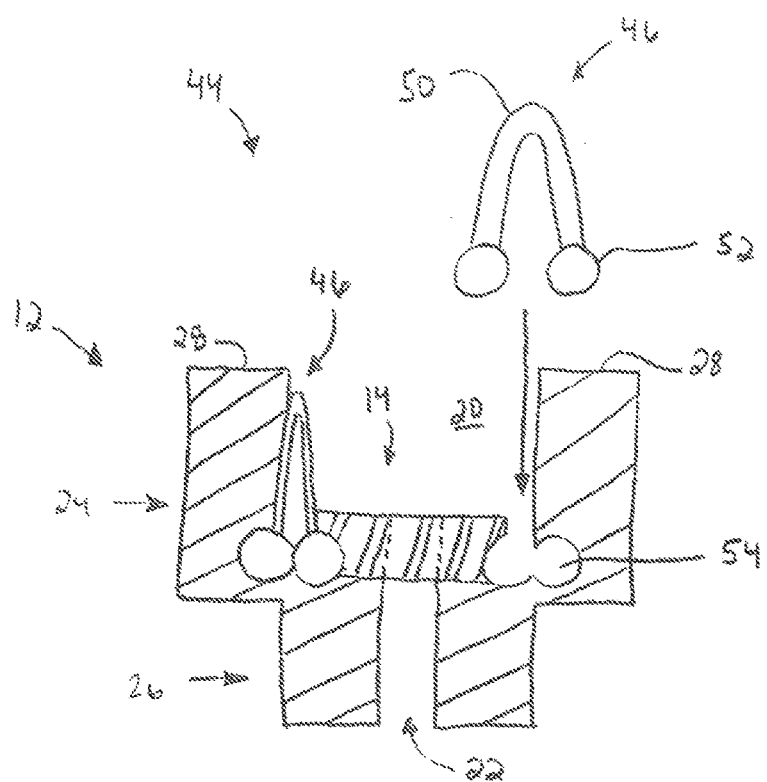
FIG. 5 is a cross-sectional view showing a locking mechanism adapted to secure the fastener in FIG. 4B to the implantable body.

The stereotactic guide assembly 10 can additionally or optionally include a locking mechanism 44 (FIG. 5) configured to engage the fastener 14 and prevent or minimize movement of the fastener (and thus a medical device) when the fastener is seated within the implantable body 12. In some instances, the locking mechanism 44 can comprise a plurality of locks 46 configured to engage the fastener 14 and ensure that the fastener does not rotate or back out of the interior chamber 20 of the implantable body 12. Each lock 46 can be wedged between an inner surface 48 of interior chamber 20 and the outer surface 40 of fastener 14. In one example, each lock 46 can have a C-shaped configuration and include a curved portion 50 and enlarged end portions 52 that fit into complementary grooves 54 of the fastener 14 and the interior chamber 20. The end portions 52 are illustrated in FIG. 5 as having a spherical or bulbous shape; however, it will be appreciated that the end portions can have other shapes (e.g., a spherical plug, a conical shaped cork, a cylindrical peg) so long as each lock 46 performs its desired function. It will also be appreciated that the fastener 14 and the interior chamber 20 need not have threads or grooves to accept a portion of each lock 46 so long as the lock(s) prevent(s) the fastener from rotating or otherwise disengaging from the external coupling feature 32 during use of the stereotactic guide assembly 10.

Figure 6A:
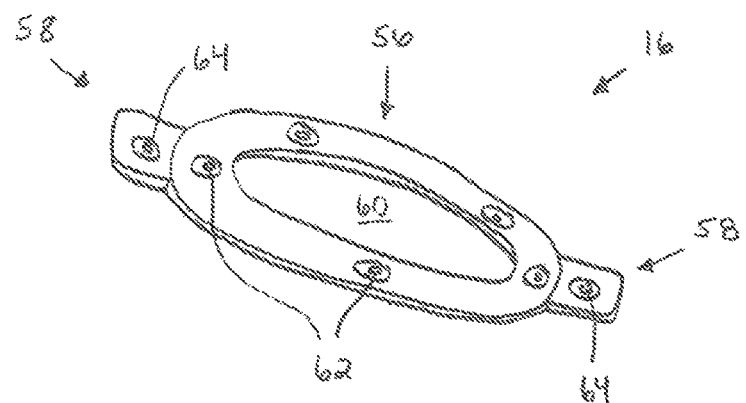
FIG. 6A is a perspective view showing a cranial fixation ring comprising the stereotactic guide assembly in FIGS. 1A-C.
Figure 6B:
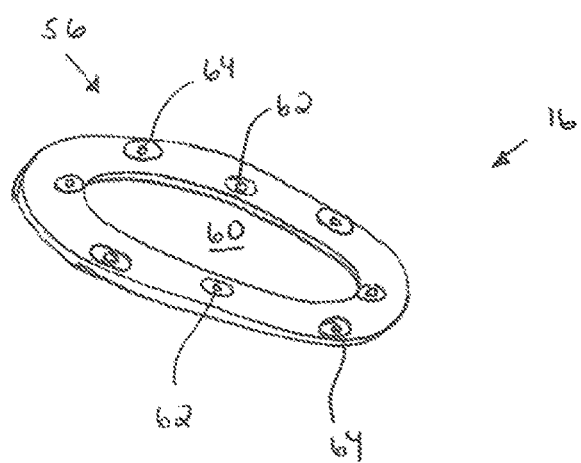
FIG. 6B is a perspective view showing an alternative construction of the cranial fixation ring in FIG. 6A.

Another aspect of the stereotactic guide assembly 10 can include a cranial fixation ring 16 (FIGS. 6A-B). The cranial fixation ring 16 can be sized and dimensioned to facilitate attachment of the implantable body 12 to the cranium of a subject (and within a burr hole associated therewith). As shown in FIG. 6A, the cranial fixation ring 16 can comprise a guide portion 56 adapted to mate with the upper receiving surface 28 of the implantable body 12, and a plurality of radially spaced apart attachment members 58. Each of the attachment members 58 can be connected to the guide portion 56 (e.g., integrally formed therewith) and adapted to contact separate portions of the cranium adjacent the burr hole. As shown in FIG. 6A, the guide portion 56 can be ring-shaped and include a central opening 60 configured to receive the implantable body 12. The guide portion 56 can include one or more apertures 62, each of which is adapted to receive a fastening mechanism, such as a screw. The apertures 62 can be sized and dimensioned so that they are in registration with corresponding channels (not shown) of the implantable body 12 when the cranial fixation ring 16 is mated with the implantable body. Each of the attachment members 58 can also include an aperture 64 adapted to receive a fastening mechanism for anchoring the cranial fixation ring 16 to the cranium. The cranial fixation ring 16 can be fabricated from one or a variety of biocompatible materials (e.g., a polymeric material).

An alternative construction of the cranial fixation ring 16 is shown in FIG. 6B. In this embodiment, the cranial fixation ring 16 can comprise a guide portion 56 adapted to mate with the upper receiving surface 28 of the implantable body 12. Unlike the cranial fixation ring 16 shown in FIG. 6A, the cranial fixation ring in FIG. 6B does not include a plurality of radially spaced apart attachment members 58. As shown in FIG. 6B, the guide portion 56 can be ring-shaped and include a central opening 60 configured to receive the implantable body 12. The guide portion 56 can include one or more apertures 62 (e.g., four apertures), each of which is adapted to receive a fastening mechanism, such as a screw. The apertures 62 can be sized and dimensioned so that they are in registration with corresponding channels (not shown) of the implantable body 12 when the cranial fixation ring 16 is mated with the implantable body. The cranial fixation ring 16 can also include one or more apertures 64 (e.g., four apertures) adapted to receive a fastening mechanism for anchoring the cranial fixation ring to the cranium. The cranial fixation ring 16 can be fabricated from one or a variety of biocompatible materials (e.g., a polymeric material).

Figure 7A:
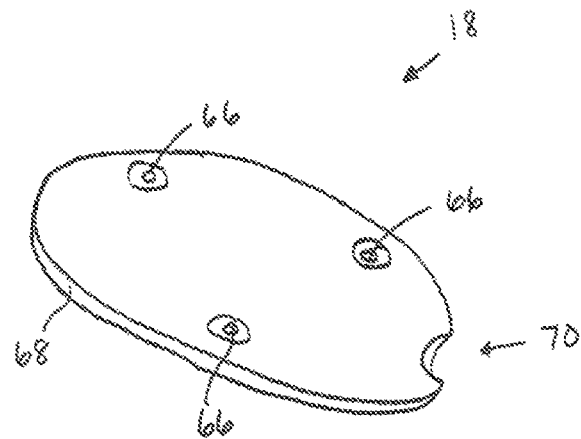
FIG. 7A is a perspective view showing a cover comprising the stereotactic guide assembly in FIGS. 1A-C.
Figure 7B:
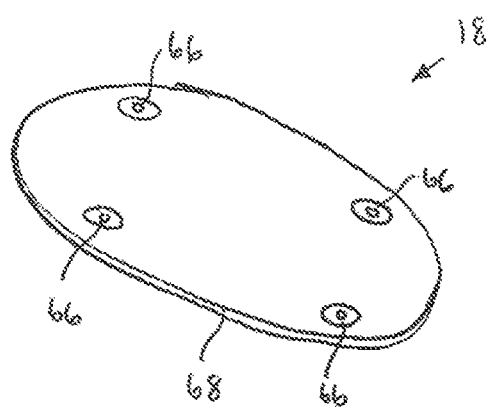
FIG. 7B is a perspective view showing an alternative construction of the cover in FIG. 7A.
Figure 8:
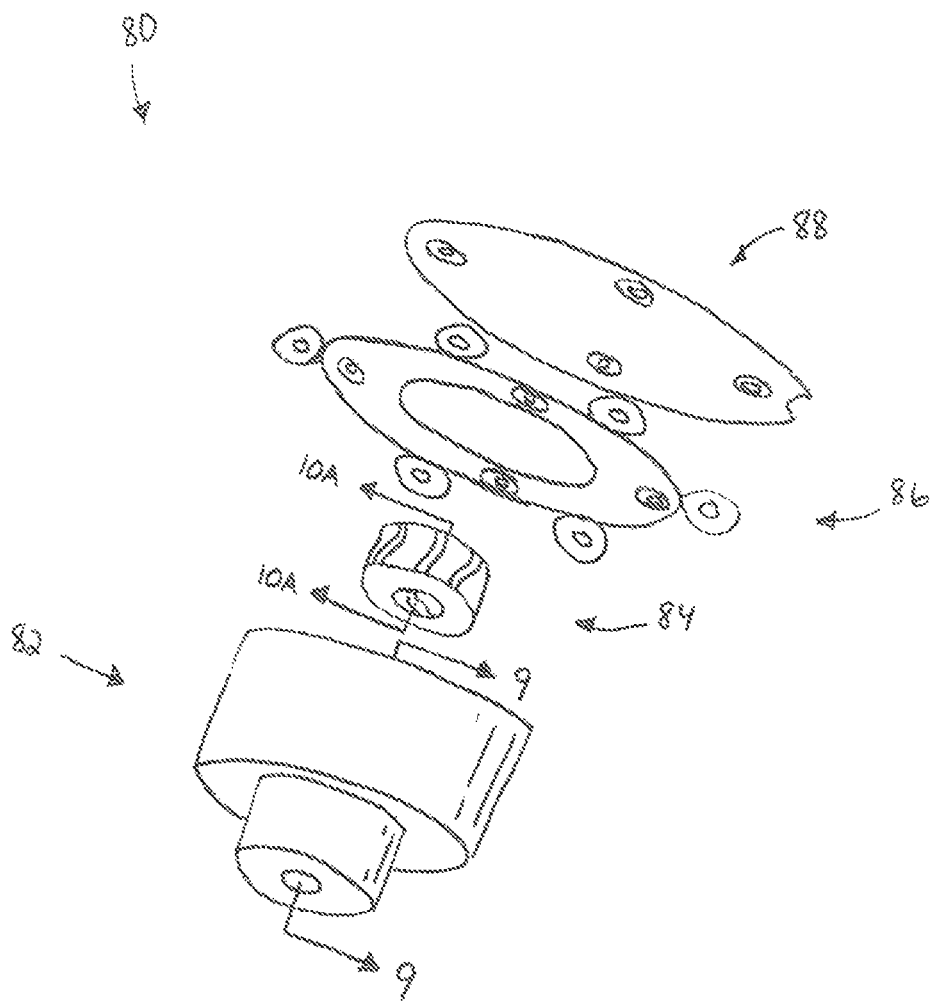
FIG. 8 is an exploded view of a stereotactic guide assembly constructed in accordance with another aspect of the present disclosure.
Figure 9:
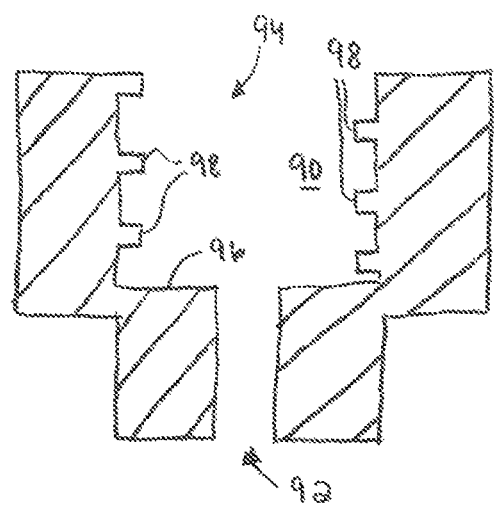
FIG. 9 is a cross-sectional view taken along Line 9-9 in FIG. 8.

Another aspect of the stereotactic guide assembly 10 can include a cover 18 (FIGS. 7A-B). One embodiment of the cover 18, shown in FIG. 7A, can be sized and dimensioned to cover the implantable body 12 after a medical device has been inserted into the stereotactic guide assembly 10 and properly positioned in the brain. The cover 18 can have an outer diameter that is greater than the outer diameter of the implantable body 12. The cover 18 can include one or more apertures 66, each of which is sized and dimensioned to receive a fastening mechanism (e.g., a screw). Each of the apertures 66 can also be configured such that the apertures 62 of the guide portion 56 are in registration with the apertures of the cover 18 when the cover is mated with the cranial fixation ring 16. The cover 18 can include a rim 68 having a notch 70 adapted to hold a medical device in place. For example, the notch 70 can be used to secure an electrical lead that has been inserted into the implantable body 12. The cover 18 can be made from one or a combination of materials, such as metallic materials (e.g., titanium or stainless steel), semi-metallic materials, and polymeric materials.

An alternative construction of the cover 18 is shown in FIG. 7B. The cover 18 shown in FIG. 7B is adapted to mate with the cranial fixation ring 16 illustrated in FIG. 6B. As such, the cover 18 (FIG. 7B) can be sized and dimensioned to cover the implantable body 12 after a medical device has been inserted into the stereotactic guide assembly 10 and properly positioned in the brain. The cover 18 can have an outer diameter that is greater than the outer diameter of the implantable body 12. The cover 18 can include one or more apertures 66 (e.g., four apertures), each of which is sized and dimensioned to receive a fastening mechanism (e.g., a screw). Each of the apertures 66 can also be configured such that the apertures 64 of the guide portion 56 are in registration with the apertures of the cover 18 when the cover is mated with the cranial fixation ring 16 (FIG. 6B). Although not shown in FIG. 7B, the cover 18 can include a rim 68 having a notch 70 adapted to hold a medical device in place. For example, the notch 70 can be used to secure an electrical lead that has been inserted into the implantable body 12. The cover 18 can be made from one or a combination of materials, such as metallic materials (e.g., titanium or stainless steel), semi-metallic materials, and polymeric materials.

Another example of a stereotactic guide assembly 80 according to the present disclosure is illustrated in FIGS. 8-12B. The stereotactic guide assembly 80 (FIG. 8) can comprise an implantable body 82, a fastener 84, a cranial fixation ring 86, and a cover 88. The implantable body 82 (FIG. 9) can have an interior chamber 90 and a first passageway 92 that extends through the implantable body into communication with the interior chamber. At least a portion of the interior chamber 90 can be defined by a first coupling feature 94. For example, all or only a portion of an inner surface 96 defining the interior chamber 90 can comprise a first series of threads 98. Other features of the implantable body 82 can be identical or similar to those described for the implantable body 12 (FIGS. 1A-C) above.

Figure 10A:
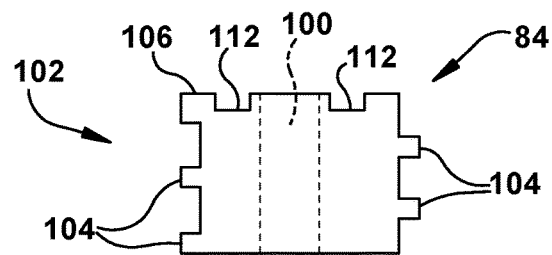
FIG. 10A is a cross-sectional view taken along Line 10A-10A in FIG. 8.
Figure 10B:
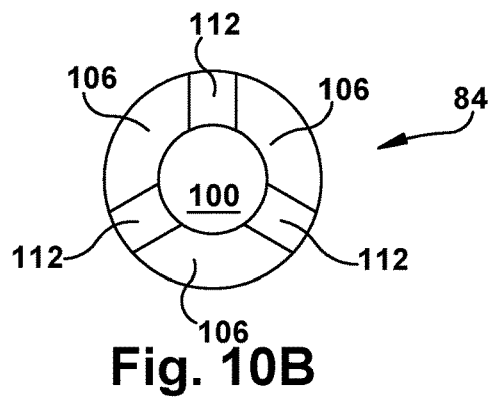
FIG. 10B is a schematic illustration showing an upper surface of a fastener in FIG. 10A.
Figure 10C:
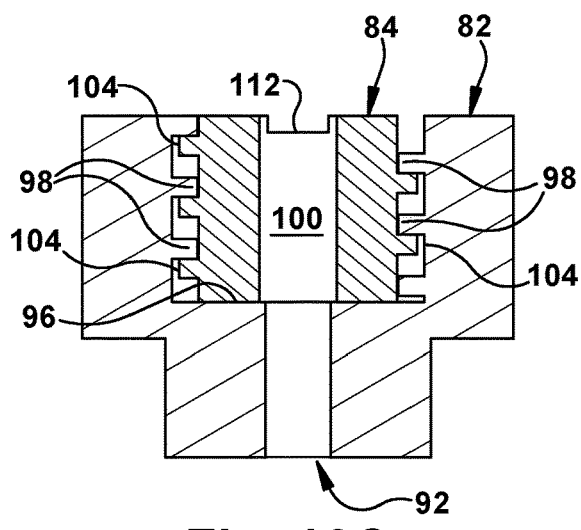
FIG. 10C is a schematic illustration depicting engagement of the first coupling feature of the upper portion of the implantable body with the second coupling feature of the fastener.
Figure 11:
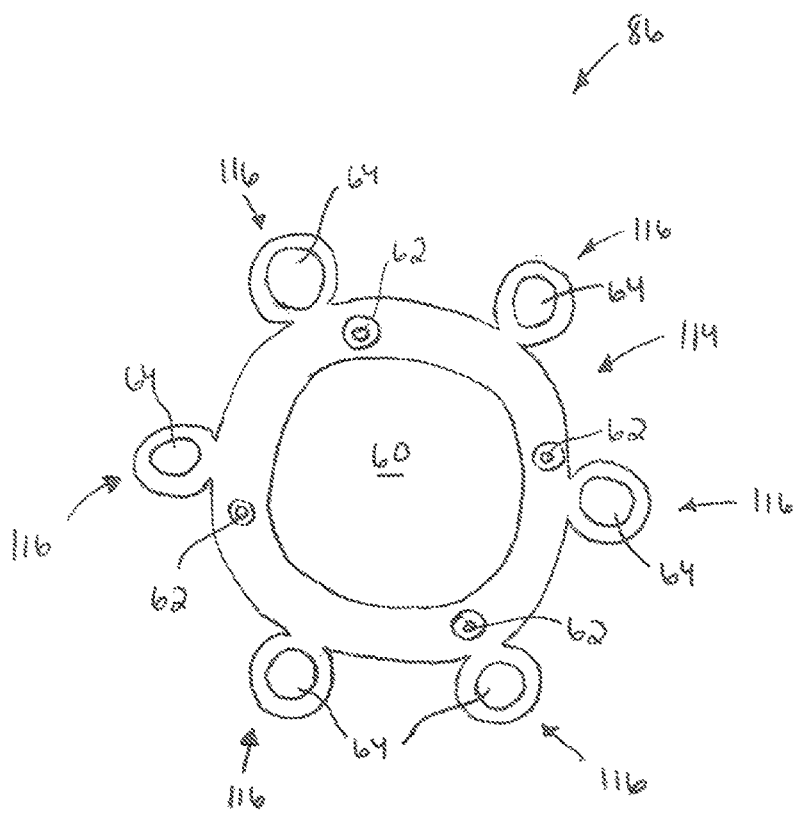
FIG. 11 is a schematic illustration of a cranial fixation ring comprising the stereotactic guide assembly in FIG. 8.

Referring to FIGS. 10A-C, the fastener 84 can be configured to fit in the interior chamber 90. The fastener 82 can have a second passageway 100 extending therethrough, and a second coupling feature 102 adapted to releasably engage the first coupling feature 94. As shown in FIG. 10A and 10C, the second coupling feature 102 can comprise a second series of threads 104 that are complementary to the first series of threads 98. The fastener 84 can also include an upper receiving surface 106 adapted to mate with a complementary surface 108 (FIGS. 12A-B) of a fastener insertion tool 110. For example, the upper receiving surface 106 (FIG. 10A) can include one or more indents or depressions 112, each of which is configured to securely mate with a complementary feature 126 of the fastener insertion tool 110. Other features of the fastener 84 can be identical or similar to the fastener 14 (FIGS. 4A-B) described above.

The cranial fixation ring 86 (FIG. 11) can be similarly configured as the cranial fixation ring 16 (FIGS. 6A-B) described above. For example, the cranial fixation ring 86 (FIG. 11) can comprise a guide portion 114 and a plurality of radially spaced apart attachment members 116 connected to the guide portion. In one example, each of the attachment members 116 can have a circular configuration and include an aperture 62 for receiving a fastening mechanism (e.g., a screw). Other features of the cranial fixation ring 86 can be identical or similar to the cranial fixation ring 16 (FIGS. 6A-B) described above.

Figure 12A:
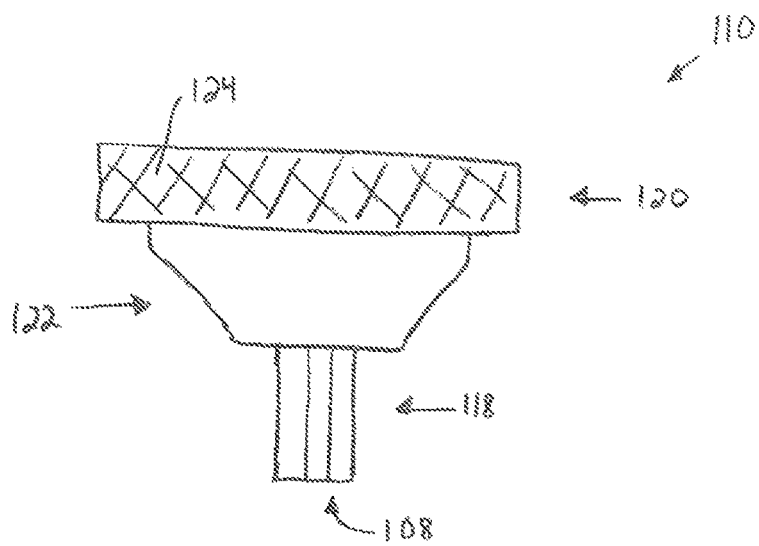
FIG. 12A is a schematic illustration showing a fastener insertion tool constructed in accordance with another aspect of the present disclosure.
Figure 12B:
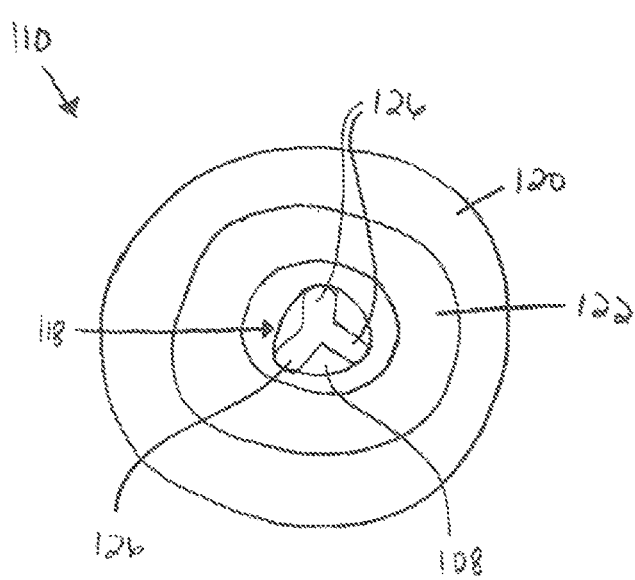
FIG. 12B is a schematic illustration showing a view from a bottom end of the fastener insertion tool in FIG. 12A.

Another aspect of the present disclosure can include a fastener insertion tool 110 (FIGS. 12A-B) for use with the stereotactic guide assembly 80. The fastener insertion tool 110 can be used to secure the fastener 84 within the implantable body 82. As shown in FIGS. 12A-B, the fastener insertion tool 110 can comprise a stem portion 118 that is connected to a handle portion 120 via an intermediate section 122. The handle portion 120 can have a disk-shaped configuration and be adapted for grasping by a user. A peripheral surface 124 of the handle portion 120 can include an etched pattern (e.g., a series of grooves or lines) (indicated by cross-hatch in FIG. 12A) to facilitate tactile control of the tool 110. The intermediate section 122 can have a frusto-conical shape and extend between the handle portion 120 and the stem portion 118. The stem portion 118 can have a cylindrical configuration and include a complementary surface 108 adapted to mate with the upper receiving surface 106 of the fastener 84. As discussed above, for example, the complementary surface 108 can include one more features 126 (e.g., pre-shaped teeth or protrusions) adapted to mate with the indents 112 or depressions comprising the upper receiving surface 106 of the fastener 84. All or only a portion of the tool 110 can be made of a metal, a metal alloy (e.g., titanium, stainless steel, etc.), or a polymeric material.

Methods

Figure 13:
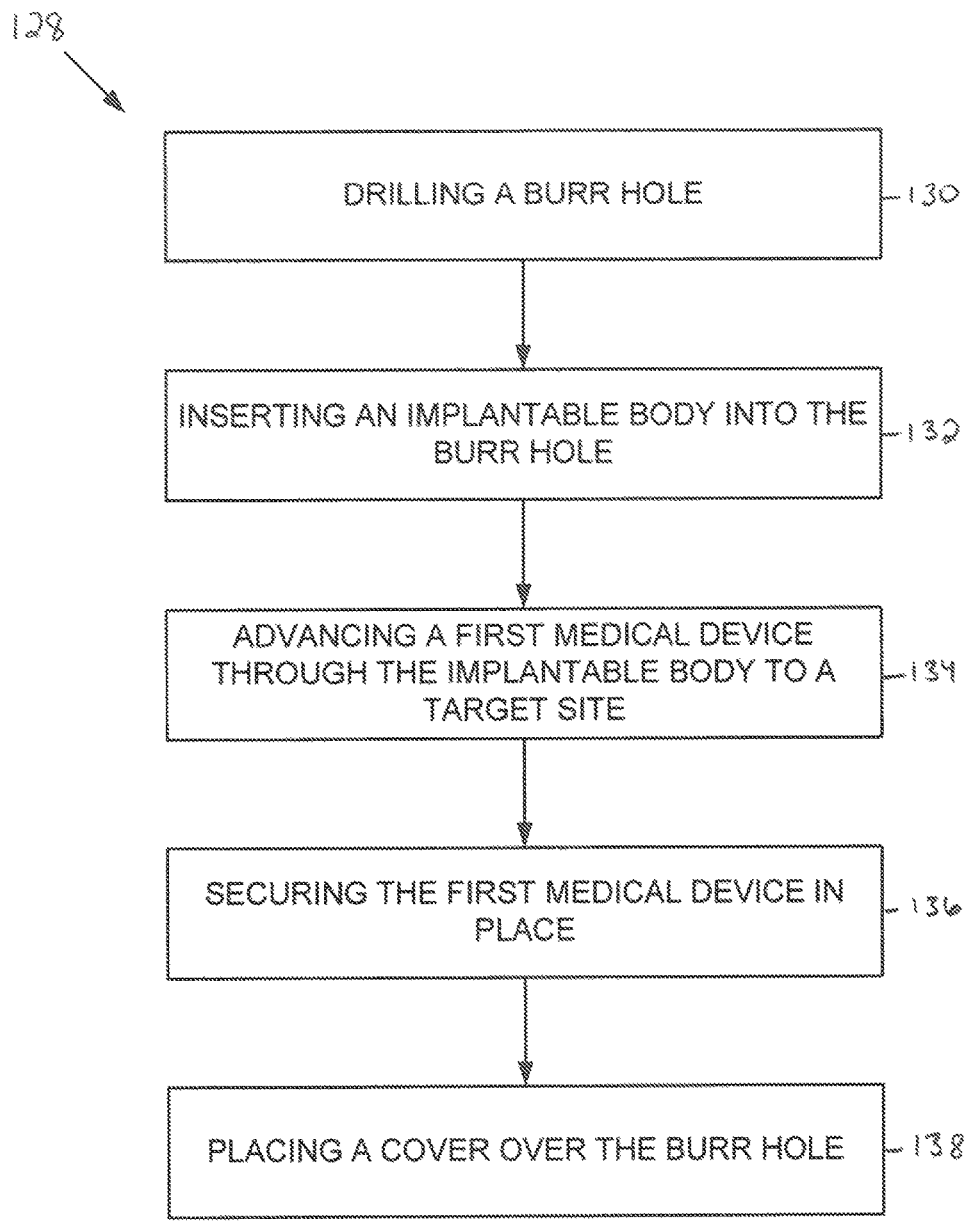
FIG. 13 is a process flow diagram illustrating a method for implanting a first medical device in a target site of a subject's brain according to another aspect of the present disclosure.

Another aspect of the present disclosure can include a method 128 (FIG. 13) for implanting a first medical device in a target site of a brain of a subject. The method 128 can find use in a variety of stereotactic procedures including, but not limited to, hydrocephalus, electrical stimulation (e.g., deep brain stimulation), brain tumor treatment and/or analysis, ablation, biopsy, lesioning, intra-cerebral chemical and/or biological agent injection, and combinations thereof. As shown in FIG. 13, the method 128 can generally comprise the steps of: drilling a burr hole in a cranium of a subject (Step 130); inserting an implantable body into the burr hole (Step 132); advancing a first medical device through the first passageway of the implantable body to the target site (Step 134); securing the first medical device in place (Step 136); and placing a cover over the burr hole (Step 138). Although the method 128 is described below using the stereotactic guide assembly 10 illustrated in FIGS. 1A-C, it will be appreciated that any other embodiment of the stereotactic guide assembly (or combination of embodiments) described herein can be used with the method.

Prior to Step 130, standard pre-operative care can be administered to the subject. For example, head fiducial markers (e.g., scalp or skull fiducial markers) can be placed on the head of the subject. A pre-operative MRI (volumetric T1) can then be taken, whereafter the trajectory to the target site is determined using stereotactic software (e.g. the target site, the entry point, and the trajectory to the target site can be determined). The subject can then be anesthetized and positioned on an operating table. The fiducial markers may then be registered, and the entry point marked on the scalp of the subject using a frameless wand (for frameless procedures) or pins (for a framed procedure). Preparation and draping can then be performed according to standard procedure. A small incision in the scalp of the subject, which is centered in the previously-marked entry point, can then be made.

At Step 130, a burr hole can be drilled in the cranium 140 of the subject (at the entry point) using a specific drill bit. The dura can then be opened using standard procedures. Next, the implantable body 12 of the stereotactic guide assembly 10 can be lowered into the burr hole (Step 132). The implantable body 12 can be held in place by an implantation device (e.g., a robot, a stereotactic microframe, etc.) (not shown). A cannula (not shown) can then be inserted through the first passageway 22 of the implantable body 12. If necessary, a stylet (not shown) can be removed from the cannula. The trajectory to the target site can then be verified using a frameless wand or robotic arm (not shown). Alternatively, after the trajectory to the target site is verified, micro or semi-macroelectrodes (not shown) can be advanced into the brain and the subject's physiological response assessed. If it is determined that the target site is incorrect based on the subject's physiological response, the electrodes can be removed, the stereotactic coordinates re-positioned, and the electrodes advanced into the subject's brain once again. The subject's physiological response can then be assessed to ensure the target site is correct. Next, the implantable body 12 can be screwed into the skull 140 (if the implantable body is externally threaded), or the cranial fixation ring 16 can be mated with the implantable body and the cranial fixation ring then screwed into the cranium of the subject.

Figure 14:
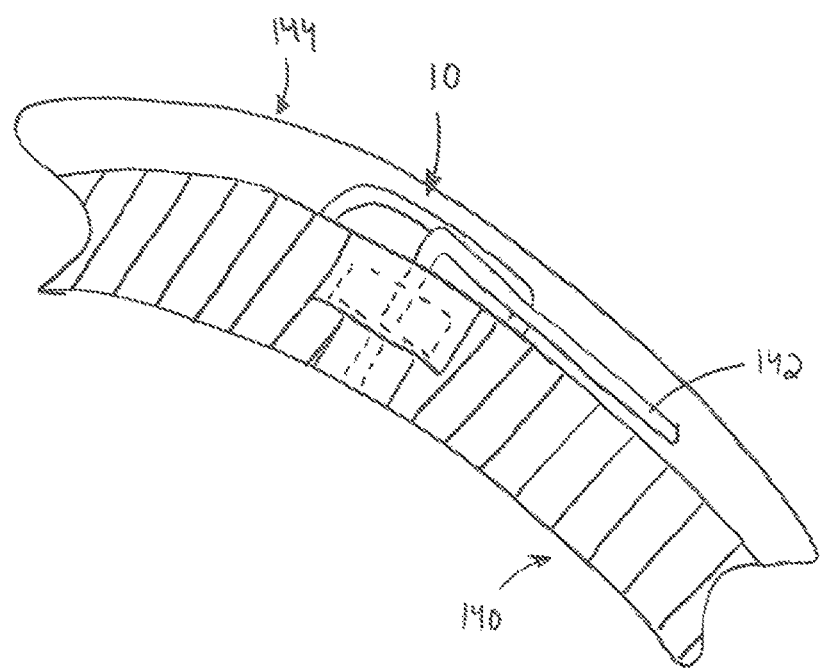
FIG. 14 is a schematic illustration showing a stereotactic guide assembly inserted in the head of subject.

After securing the implantable body 12 in the burr hole, the cannula can be removed from the implantable body. At Step 134, a first medical device 142 (FIG. 14) (e.g., an electrical lead) can then be inserted through the first passageway 22 of the implantable body 12 into the target site. The first medical device 142 can be secured in place by threading the fastener 14 over the first medical device, and mating the internal coupling feature 38 of the fastener with the external coupling feature 32 of the implantable body 12 (Step 136). At Step 138, the cover 18 is placed under the skin 144 of the subject so that it covers the implantable body 12 and the cranial fixation ring 16. The cover 18 is also placed so that the first medical device 142 is seated within, and extends through, the notch 70 of the cover. The cover 18 can then be secured to the implantable body 12 either directly or via the cranial fixation ring 16. Once the stereotactic guide assembly 10 is fully implanted in the subject, the skin 144 can be closed and the operation completed as shown in FIG. 14.

Figure 15:
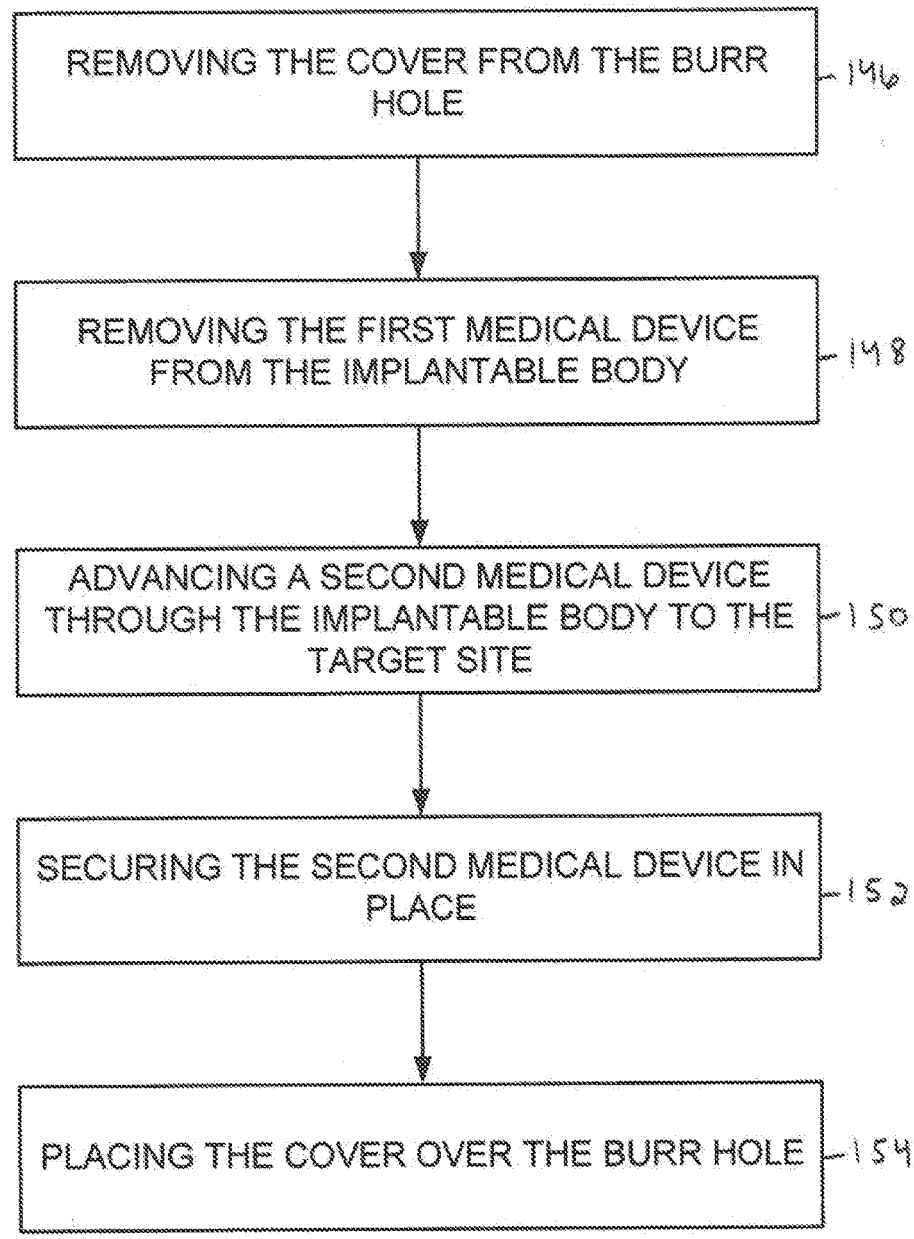
FIG. 15 is a process flow diagram illustrating a method for replacing the first medical device with a second medical device according to another aspect of the present disclosure.

In some instances, the method 128 can further include Steps 146-154 (FIG. 15) where a surgical revision is necessary, or if a second different medical device (not shown) is otherwise to be implanted or inserted at the target site. In such instances, the cover 18 can be removed from the skin 144 of the subject (Step 146) and the fastener 14 disengaged or uncoupled from the implantable body 12. At Step 148, the indwelling first medical device 142 can then be removed from the subject. Next, the second medical device can be advanced through the implantable body 12 (Step 150) and secured therein via the fastener 14 (Step 152). At Step 154, the cover 18 can be placed back in the subject's skin 144 over the burr hole to cover the stereotactic guide assembly 10. Once again, the cover 18 can be secured to the implantable body 12 so that the second medical device is securely seated within, and extends through, the notch 70 of the cover. Advantageously, after implantation, the stereotactic guide assembly 10 can provide a base for future surgical trajectories to a target site and allow for interchangeability of other medical devices that can be positioned at the target site.

In one example, the method 128 can find use in treating a patient with hydrocephalus. About 160,000 ventriculoperitoneal shunts are implanted each year to treat patients with hydrocephalus; yet, approximately 50% of the shunts fail within two years. Revision surgery requires a complex secondary procedure that is costly and exposes patients to increased risk of infection, among other potential complications. Advantageously, the method 128 permits implantation of the surgical guide assembly 10 to provide a base for future surgical trajectories to a target site and allow for interchangeability of ventriculoperitoneal shunts that can be positioned at the target site. Following completion of the method 128, for instance, the surgical guide assembly 10 can remain in a burr hole such that only the ventriculoperitoneal shunt (and/or a cannula associated therewith) and the cover 18 need be replaced. Consequently, the method 128 can significantly reduce the cost and risks associated with revision procedures, e.g., by reducing both surgical time and general anesthesia time.

From the above description of the disclosure, those skilled in the art will perceive improvements, changes and modifications. Such improvements, changes, and modifications are within the skill of the art and are intended to be covered by the appended claims. All patents, patent applications, and publications cited herein are incorporated by reference in their entirety.

The following is claimed:

1. A stereotactic guide assembly comprising:
   an implantable body having an interior chamber and a first passageway that extends through the implantable body into communication with the interior chamber, the implantable body having a stepped-down configuration wherein the implantable body comprises an upper portion connected to a lower portion, the upper portion at least partially defined by a first coupling feature and having an outer diameter greater than an outer diameter of the lower portion, the implantable body sized and dimensioned to fit within a burr hole located in a cranium of a human subject; and
   a fastener configured to fit in the interior chamber, the fastener having a second passageway extending therethrough and a second coupling feature adapted to releasably engage the first coupling feature.

2. The stereotactic guide assembly of claim 1, wherein the portion of the interior chamber defined by a first coupling feature comprises a first series of threads, and the second coupling feature comprises a second series of threads that are complementary to the first series of threads.

3. The stereotactic guide assembly of claim 1, wherein the fastener further includes an upper receiving surface adapted to mate with a complementary surface of a fastener insertion tool.

4. The stereotactic guide assembly of claim 1, further comprising a cranial fixation ring adapted to mate with the implantable body and thereby secure the implantable body within a burr hole.

5. The stereotactic guide assembly of claim 4, wherein the cranial fixation ring further comprises: a guide portion adapted to mate with an upper surface of the implantable body; and a plurality of radially spaced apart attachment members, each of which is connected to the guide portion and adapted to contact separate portions of a cranium located adjacent the burr hole.

6. A stereotactic guide assembly comprising:
   an implantable body having an interior chamber and a first passageway that extends through the implantable body into communication with the interior chamber, the implantable body having a stepped-down configuration wherein the implantable body comprises an upper portion connected to a lower portion, the upper portion at least partially defined by an external coupling feature and having an outer diameter greater than an outer diameter of the lower portion, the implantable body sized and dimensioned to fit within a burr hole located in a cranium of a human subject; and
   a fastener configured to fit in the interior chamber, the fastener having a second passageway extending therethrough and an internal coupling feature adapted to releasably engage the external coupling feature.

7. The stereotactic guide assembly of claim 6, wherein the external coupling feature is a threaded section that is complementary to a threaded section of the internal coupling feature.

8. The stereotactic guide assembly of claim 6, wherein an upper portion of the external coupling feature has a beveled edge.

9. The stereotactic guide assembly of claim 6, wherein an outer surface of the fastener and an inner surface of the interior chamber are threaded.

10. The stereotactic guide assembly of claim 6, further comprising a sealing ring configured to fit within the second passageway of the fastener.

11. The stereotactic guide assembly of claim 6, further comprising a cover that is sized and dimensioned to cover the implantable body when implanted in a burr hole.

12. The stereotactic guide assembly of claim 11, wherein the cover includes a rim having a notch adapted to receive an electrical lead.

13. The stereotactic guide assembly of claim 6, further comprising a locking mechanism configured to engage the fastener and prevent or minimize movement of the fastener when the fastener is seated within the implantable body.

14. The stereotactic guide assembly of claim 13, wherein the locking mechanism comprises a plurality of C-shaped clips adapted to separately wedge between an inner surface of the interior chamber and an outer surface of the fastener.

* * * * *